United States Patent
Hull et al.

(10) Patent No.: US 8,392,133 B1
(45) Date of Patent: Mar. 5, 2013

(54) METHOD FOR MEASURING SHEAR WAVESPEED IN AN ISOTROPIC PLATE

(75) Inventors: Andrew J. Hull, Portsmouth, RI (US); Benjamin A. Cray, West Kingston, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 284 days.

(21) Appl. No.: 12/824,563

(22) Filed: Jun. 28, 2010

(51) Int. Cl.
*G01R 23/00* (2006.01)
*G01R 23/16* (2006.01)

(52) U.S. Cl. .......................... 702/75; 702/77
(58) Field of Classification Search .............. 702/75, 702/77
See application file for complete search history.

(56) References Cited

U.S. PATENT DOCUMENTS

| | | | | |
|---|---|---|---|---|
| 5,327,358 A | * | 7/1994 | Stubbs | 702/36 |
| 6,005,916 A | * | 12/1999 | Johnson et al. | 378/87 |
| 6,848,311 B1 | * | 2/2005 | Hull | 73/579 |
| 7,330,799 B2 | * | 2/2008 | Lefebvre et al. | 702/75 |
| 2004/0065152 A1 | * | 4/2004 | Hull | 73/579 |
| 2009/0007671 A1 | * | 1/2009 | Hull | 73/579 |
| 2009/0056453 A1 | * | 3/2009 | McAleavey | 73/597 |

* cited by examiner

*Primary Examiner* — Michael Nghiem
(74) *Attorney, Agent, or Firm* — James M. Kasischke; Michael P. Stanley; Jean-Paul A. Stanley

(57) ABSTRACT

Using a mechanical shaker test the shear wavespeed in a plate is estimated by applying a cyclical point force to the plate, measuring normal velocity of waves caused by the force, transforming temporal domain measurements with a Fourier transform into a frequency domain, transforming spatial domain measurements into a $\{k_x,k_y\}$ wavevector domain spectra using Fourier transforms, determining propagation wavenumbers for given Lamb waves from peaks within the $\{k_x,k_y\}$ spectra, and determining shear wavespeed by applying a Newton-Raphson gradient method using the propagation wavenumbers to Raleigh-Lamb dispersion curve equations.

6 Claims, 6 Drawing Sheets

METHOD FOR MEASURING SHEAR WAVESPEED IN AN ISOTROPIC PLATE

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

BACKGROUND OF THE INVENTION (1) Field of the Invention

The present invention is generally directed towards a method to measure the shear wavespeed in an isotropic plate. More specifically, the invention is directed towards a method to estimate the shear wavespeed of a plate shaped test specimen using a mechanical shaker test.

(2) Description of the Prior Art

The shear wave, S-wave or secondary wave, is one of the two main types of elastic body waves, a type of seismic wave, that moves through the body of an object, unlike surface waves. The shear wave moves as a shear or transverse wave, so motion is perpendicular or normal to the direction of wave propagation. The shear wave moves through elastic media, and the main restoring force comes from shear effects. These waves are divergenceless.

Measurement of material properties of elastic systems has been and continues to be an active area of investigation. Resonant techniques have been used that usually involve measuring the natural resonant frequencies of slender structures. Once measured, these frequencies are equated to the corresponding analytical natural frequencies, which are typically functions of Young's modulus, shear modulus, length and/or mass. The resultant expression can be solved, which produces an estimate of Young's or shear modulus at each natural frequency. Non-resonant methods have also been used. Although slightly more complicated than resonant techniques, these methods have the ability to estimate material properties at frequencies other than the natural frequency of the system. Typically, non-resonant techniques involve equating measured data with a simplified analytical model of the system. The analytical model is rewritten so that the material properties that are to be estimated are rendered as functions of the data.

Both resonant and non-resonant methods are usually performed at low frequencies, where simple (though limited) analytical models and corresponding dynamic behavior exists. Ideally, the structure under testing will have only a single mode of energy propagation, so that the effects of other wave motion will not corrupt the estimation process.

Few wavespeed estimation techniques have been developed for general plates and beams. Most of the research has assumed thin plate (or beam) behavior where the theory is that of a single flexural wave propagating in the structure. The estimation of Young's modulus and shear modulus have been accomplished by matching the theoretical eigen-frequencies of a Timoshenko beam model to measured data and then deducing the material parameters. Some techniques at ultrasonic frequencies have been derived, in order to support the medical imaging or the aviation industry. The measurement of elastic constants of thin immersed anisotropic plates has been undertaken using the identification of transmission zeros and poles based on various incident angles of an incoming ultrasonic wave. The estimation of stiffness and damping properties of viscoelastic materials by numerically inverting the transmitted ultrasonic field of an immersed thin plate at different incident angles has been accomplished.

A method has been devised to identify Lamé constants, thickness, density, longitudinal and shear attenuation and interfacial properties of a solid layer placed between two other layers. This method uses normal and angular ultrasonic reflectivity from the middle layer. The last three references involve modeling and measurement in the MHz region. Many indentation material testing methods exist. These usually consist of loading a location of the material and measuring the resultant force and depth. Using these measurements, one can determine Young's modulus and shear modulus. These methods are usually quasi-static and frequency independent.

The elastic plate theory has been extensively developed, though thick plates have traditionally not been used to measure material properties because they support multiple wave types, and any measurement technique has to have the ability to discern between each wave type and its contribution to the measurement. Transfer function methods that measure one output (at a single location) versus a fixed input do not have the capability to separate various wave types and their associated response levels.

SUMMARY OF THE INVENTION

Accordingly, it is an object of the present invention to estimate the shear wavespeed of a plate shaped test specimen using a mechanical shaker test. This shaker test is accomplished by hanging the plate from a frame and attaching a mechanical shaker to one of the plate faces near the middle of the plate. Once this is done, the plate is shaken at various frequencies and the resulting wavenumber corresponding to specific wave motion is identified. These wavenumbers are then used in the dispersion equations for a plate to estimate the shear wavespeed.

Shaker tests are mechanical tests that are used to excite motion in different types of structures. Typically, some form of measurement is concurrently taken during the test so that data can be analyzed. Laser velocimeters that measure the velocity of the structure and accelerometers that measure the acceleration are employed to collect the data. Once this is accomplished, insight into the structures response due to varying mechanical loading conditions can be determined. Testing simple structures such as plates, beams and shells is useful because analytical solutions of their responses have been derived and direct comparison between predicted response and actual response can be achieved.

The shear wavespeed is measured in a plate in the region where dilatational and shear wavelengths begin to approach the plate thickness, i.e., fully elastic dynamic behavior. The plate is mechanically excited by a point force at a fixed frequency while simultaneously measuring the normal velocity of the plate across its entire surface. These spatial domain measurements are transferred into a wavevector two-wavenumber $(k_x, k_y)$ domain by means of two Fourier transforms. Individual waves are identified in this domain, and the resulting wave propagation wavenumbers are accurately estimated. Once they are measured, the estimated wavenumbers are inserted into a Newton-Raphson iterative solver applied to the theoretical Rayleigh-Lamb equations for the propagation of waves in a plate with traction-free boundary conditions.

Results of estimates of the squares of the shear wavenumbers are thus obtained, allowing for calculations of the shear wavespeed.

Other objects and advantages of the present invention will become apparent in accordance with the present invention as claimed.

DETAILED DESCRIPTION OF THE INVENTION

Figure 1:
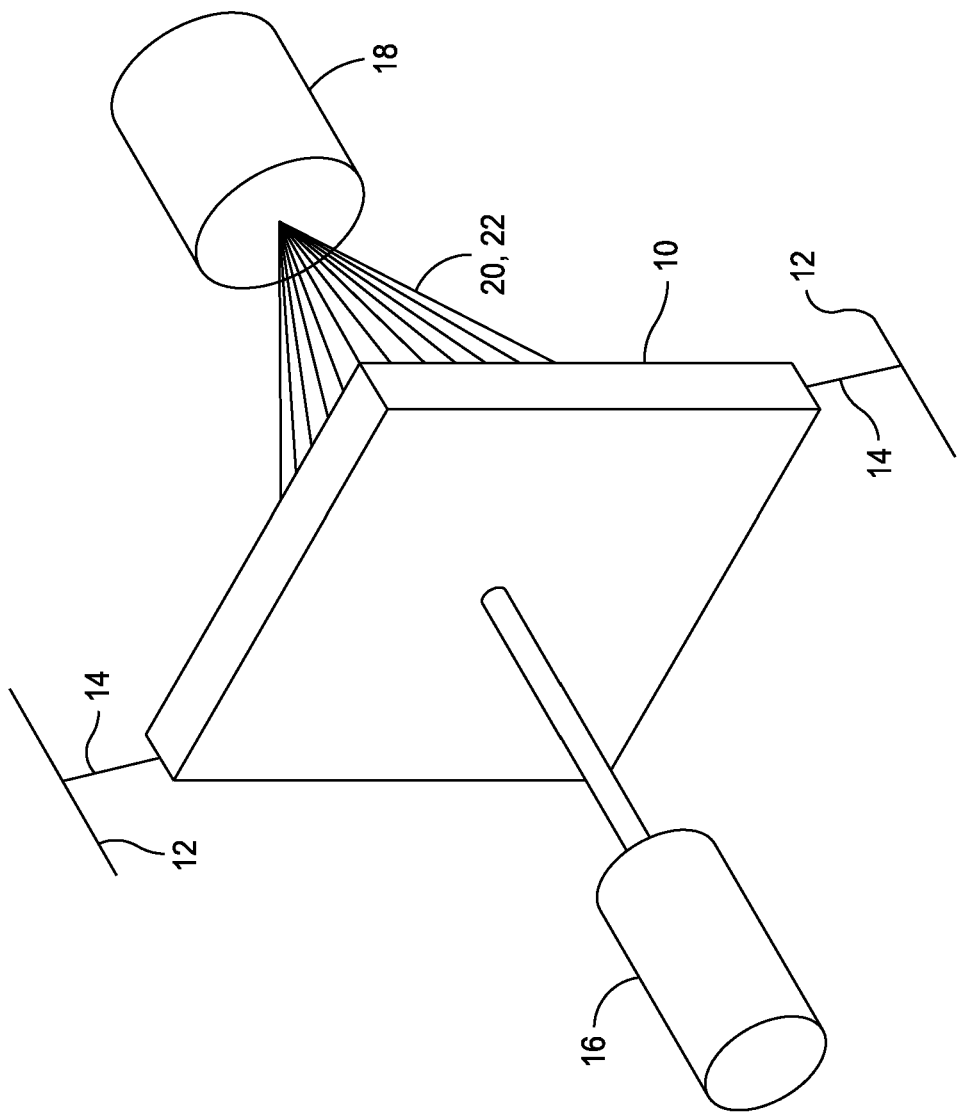
FIG. 1 is a diagram of an experimental test setup for use of the current method.

A possible experimental setup for the present method is given in FIG. 1. A test plate 10 is joined to a structure or fixed frame 12 by resilient cords 14. Two corner supports are shown in the drawing, but more supports could be present. Plate 10 is preferably around 1 inch thick; however, almost any thickness can be used. Thinner plates lose vibration modes. Thicker plates lose vibration through losses in lossy materials such as resilient materials like plastic and rubber. Resilient cords 14 can be any elastic cord or spring providing sufficient elasticity to avoid affecting plate 10 vibration. A shaker 16 is joined to the center of plate 10. Shaker 16 can be an electromagnetic or mechanical shaker that is capable supporting the frequencies of interest. Shaker 16 should be joined to plate 10 at a single point. A laser vibrometer 18 is positioned on the opposite side of plate 10 allowing measurement of vibrations from the entire surface of plate 10. Vibrometer 18 provides a beam 20 and detects reflections 22 of the beam. Through timing and Doppler measurements, the position and velocity of the plate 10 can be determined relative to the vibrometer 18. Laser vibrometer 18 can take measurements at multiple points on the plate 10. Vibrometer 18 can be moved in relation to the plate 10 to provide orthogonal measurements or measurements can be modified in order to make them orthogonal.

The theory of wave motion in isotropic elastic thick plates is extensively developed. The objective of this invention is to estimate the shear wavespeed using the theoretical Rayleigh-Lamb equations developed for free-free plate boundary conditions. Free-free plate boundary conditions correspond to the case of traction-free boundaries; i.e., the normal and shear stresses at the plate faces are zero. There are two separate Rayleigh-Lamb dispersion equations based on the symmetry of the horizontal displacement field about the mid-plane of the plate; one corresponds to symmetrical waves and the other to anti-symmetric waves. The Rayleigh-Lamb equation for the propagation of symmetric waves is written as $$f(k_d, k_s) = \frac{\tan\left[\sqrt{k_s^2 - k^2}\,(h/2)\right]}{\tan\left[\sqrt{k_d^2 - k^2}\,(h/2)\right]} + \frac{4k^2\sqrt{k_d^2 - k^2}\sqrt{k_s^2 - k^2}}{(2k^2 - k_s^2)^2} = 0, \quad (1)$$

and the Rayleigh-Lamb equation for the propagation of anti-symmetric waves is given by $$g(k_d, k_s) = \frac{\tan\left[\sqrt{k_s^2 - k^2}\,(h/2)\right]}{\tan\left[\sqrt{k_d^2 - k^2}\,(h/2)\right]} + \frac{(2k^2 - k_s^2)^2}{4k^2\sqrt{k_d^2 - k^2}\sqrt{k_s^2 - k^2}} = 0, \quad (2)$$

where h is the thickness of the plate (m), $k_s$ is the shear wavenumber (rad m$^{-1}$), $k_d$ is the dilatational wavenumber (rad m$^{-1}$), and k is the propagation wavenumber (rad m$^{-1}$). When equation (1) or (2) is satisfied, the propagation wavenumber k corresponds to a specific Lamb wave (sometimes also referred to as Rayleigh-Lamb wave) traveling in the plate. Note that equation (1) or (2) will be applicable to any specific wave in the plate, but not both. These two equations define the wavenumber-frequency dispersion curves and will be used with the identification of Lamb waves in the medium to estimate the shear wavespeed. The measurement or estimation of the propagation wavenumber of interest, k, is discussed in the next section.

The relationship between shear wavenumber and shear wavespeed is $$k_s = \frac{\omega}{c_s}, \quad (3)$$

where $\omega$ is the angular frequency (rad s$^{-1}$) and $c_s$ is the shear wavespeed (ms$^{-1}$). The relationship between dilatational wavenumber and dilatational wavespeed is $$k_d = \frac{\omega}{c_d}, \quad (4)$$

where $c_d$ is the dilatational wavespeed (m s$^{-1}$).

Figure 2A:
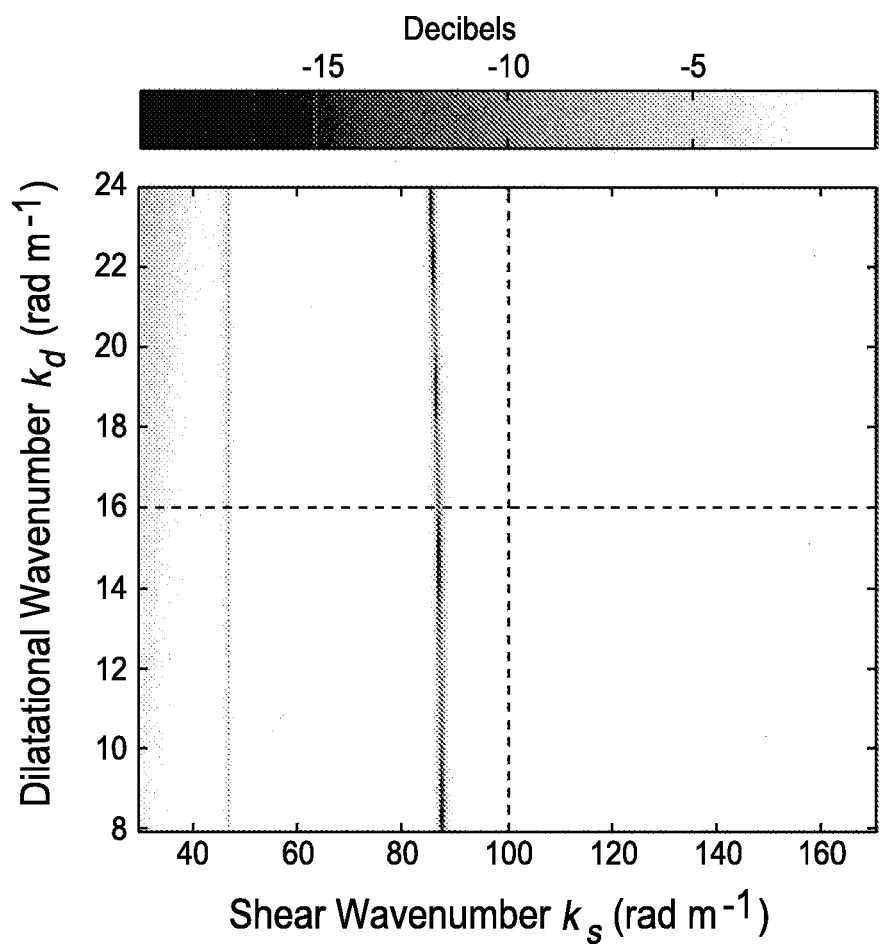
FIG. 2A is a plot of the function $f(k_d,k_s)$ versus shear and dilatational wavenumber using a propagation wavenumber of $k=46.4$ rad m$^{-1}$ displayed using a decibel scale.
Figure 2B:
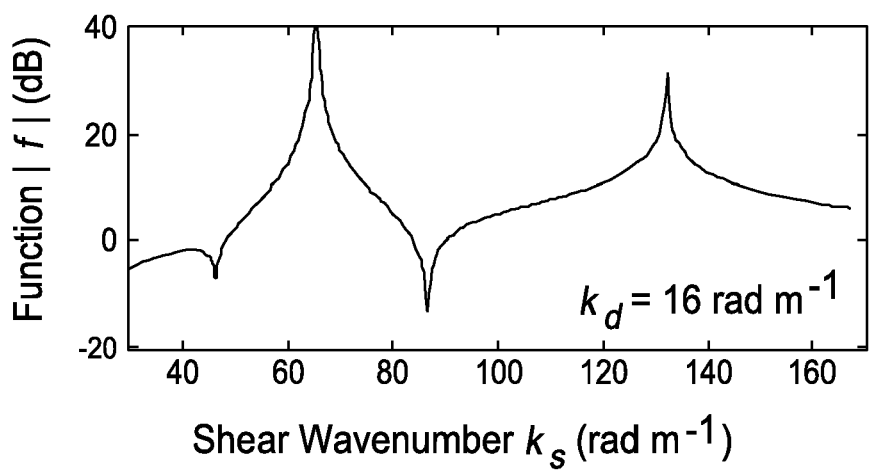
FIG. 2B is a plot of the function with respect to the shear wavenumber with the dilatational wavenumber fixed at 16 rad m$^{-1}$.
Figure 2C:
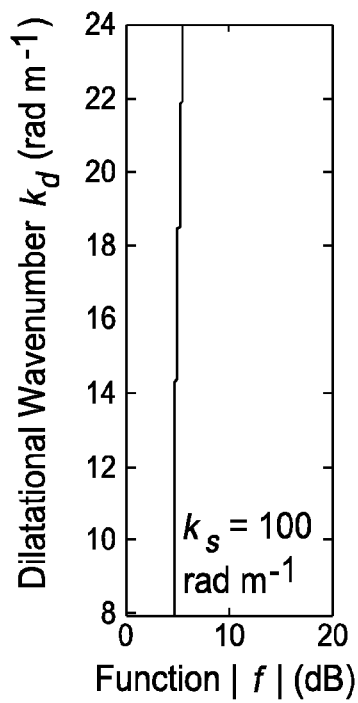
FIG. 2C is a plot of the function with respect to the dilatational wavenumber with the shear wavenumber fixed at 100 rad m$^{-1}$.

To better understand the functions $f(k_d,k_s)$ and $g(k_d,k_s)$, it is informative to display them as surfaces with respect to dilatational and shear wavenumber and examine their characteristic behavior. FIG. 2A is a plot of the function $f(k_d,k_s)$ versus shear and dilatational wavenumber using a propagation wavenumber of $k=46.4$ rad m$^{-1}$ displayed using a decibel scale. FIG. 2B is a plot of the function with respect to the shear wavenumber with the dilatational wavenumber fixed at 16 rad m$^{-1}$. FIG. 2C is a plot of the function with respect to the dilatational wavenumber with the shear wavenumber fixed at 100 rad m$^{-1}$.

Figure 3A:
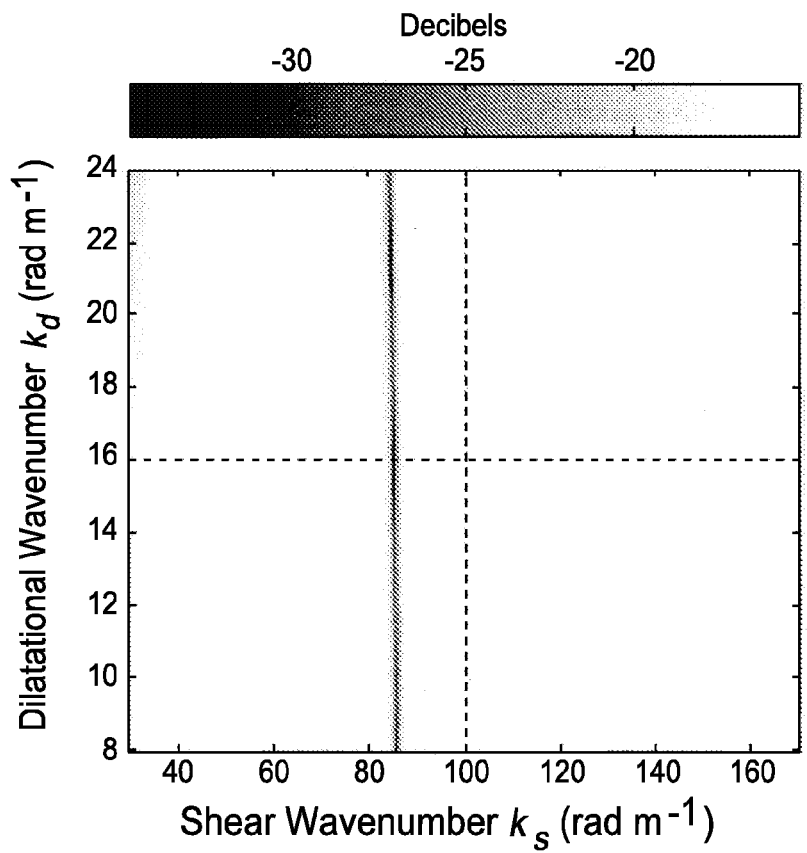
FIG. 3A is a plot of the function $g(k_d,k_s)$ versus shear and dilatational wavenumber using a propagation wavenumber of $k=107.2$ rad m$^{-1}$ displayed using a decibel scale.
Figure 3B:
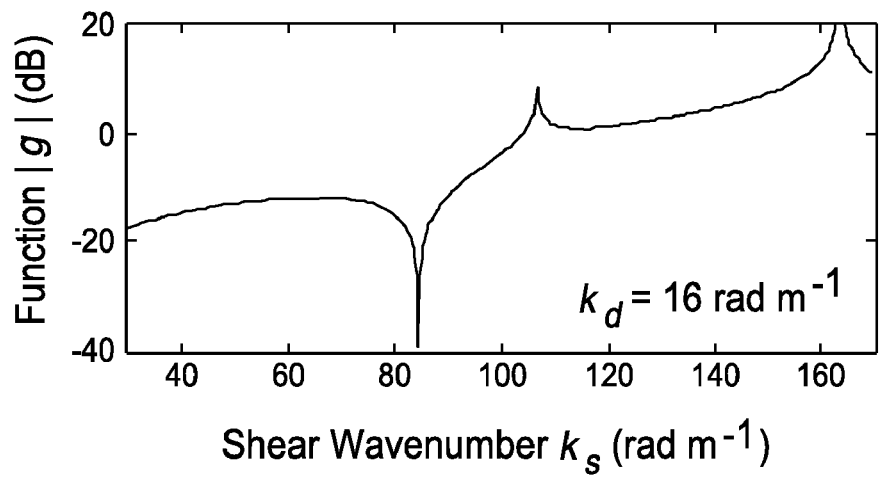
FIG. 3B is a plot of the function with respect to the shear wavenumber with the dilatational wavenumber fixed at 16 rad m$^{-1}$.
Figure 3C:
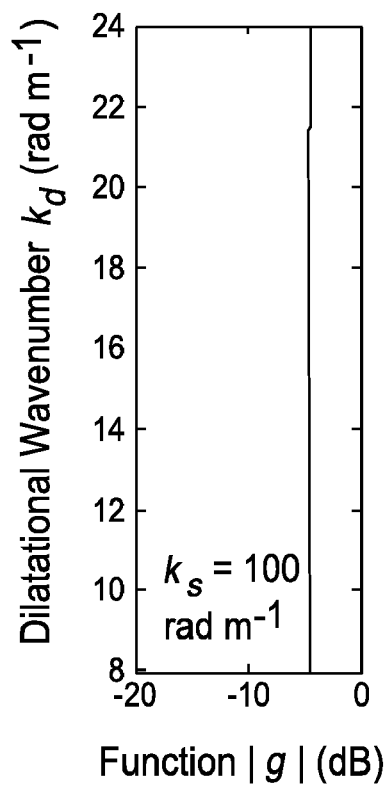
FIG. 3C is a plot of the function with respect to the dilatational wavenumber with the shear wavenumber fixed at 100 rad m$^{-1}$.

FIG. 3A is a plot of the function $g(k_d,k_s)$ versus shear and dilatational wavenumber using a propagation wavenumber of $k=107.2$ rad m$^{-1}$ displayed using a decibel scale. FIG. 3B is a plot of the function with respect to the shear wavenumber with the dilatational wavenumber fixed at 16 rad m$^{-1}$. FIG. 3C is a plot of the function with respect to the dilatational wavenumber with the shear wavenumber fixed at 100 rad m$^{-1}$.

The plate thickness h was 0.0254 m and the frequency w was $(2\pi)4000$ rad s$^{-1}$. Note that the functions vary significantly with respect to the shear wavenumber and are essentially flat with respect to the dilatational wavenumber. This overarching feature reveals two pertinent dynamic characteristics, which guide the estimation process: (1) the shear wavenumber (and, hence, the shear wavespeed) can be accurately estimated due to the well-defined minimum values of the surface with respect to the shear wavenumber; and (2) the dilatational wavenumber will be poorly estimated using this method due to the poorly defined, slowly varying minimum values of the surface with respect to the dilatational wavenumber. The estimation of the shear, wavenumber, within this region, is relatively invariant with respect to the dilatational wavenumber.

The dilatational wavespeed is assumed to be a known value and one convenient method to measure this wavespeed follows. The dilatational wavespeed was measured using an echo reduction test. An echo reduction test is accomplished by insonifying the plate and measuring the transfer function of the incident acoustic energy divided by the reflected acoustic energy. This previously developed estimation method identifies the peaks in the data and relates each specific peak to a corresponding wavelength that is a half integer multiplication of the thickness of the plate. U.S. Pat. No. 7,584,060 teaches one form of this test. When the frequencies of the relative maxima of echo reduction data are determined, they can be related to the dilatational wavespeed by $$(c_d)_n = \frac{h f_n}{n}, \tag{5}$$

where $f_n$ is the frequency of the nth relative maxima (Hz) and n is the number of wavelengths in the material that creates the relative maxima (cycles). Once this relationship is known, the dilatational wavespeed can be calculated.

It will later be analyzed how an error in the dilatational wavespeed measurement will affect the shear wavespeed measurement. Using the dilatational wavespeed measured using the method described above, the dilatational wavenumber is calculated using equation (4). The propagation wavenumber is a known quantity that can be determined either from a simulation or via experiment. With both the dilatational wavenumber and the propagation wavenumber known, a Newton-Raphson method can then be applied to equations (1) or (2) for the estimation of the shear wavenumber that generates a value of zero for the function $f(k_d,k_s)$ or $g(k_d,k_s)$. To eliminate the ambiguity of both positive and negative shear wavenumbers, the estimation process is applied to the square of the wavenumber, rather than the wavenumber itself. For equation (1) written as $f(k_d,k_s)=0$, the Newton-Raphson method yields $$[k_s^2]_{j+1} = [k_s^2]_j - \left[\frac{\partial f(k_d,k_s)}{\partial(k_s^2)}\right]_j^{-1} f(k_d,k_s)_j, \tag{6}$$

where $$\frac{\partial f(k_d,k_s)}{\partial(k_s^2)} = \frac{h\{1+\tan^2[\sqrt{k_s^2-k^2}\,(h/2)]\}}{4\sqrt{k_s^2-k^2}\tan[\sqrt{k_d^2-k^2}\,(h/2)]} + \frac{2k^2\sqrt{k_d^2-k^2}}{\sqrt{k_s^2-k^2}(2k^2-k_s^2)^2} + \frac{8k^2\sqrt{k_d^2-k^2}\sqrt{k_s^2-k^2}}{(2k^2-k_s^2)^3}. \tag{7}$$

For equation (2) written as $g(k_d,k_s)=0$, the Newton-Raphson method yields $$[k_s^2]_{j+1} = [k_s^2]_j - \left[\frac{\partial g(k_d,k_s)}{\partial(k_s^2)}\right]_j^{-1} g(k_d,k_s)_j, \tag{8}$$

where $$\frac{\partial g(k_d,k_s)}{\partial(k_s^2)} = \frac{h\{1+\tan^2[\sqrt{k_s^2-k^2}\,(h/2)]\}}{4\sqrt{k_s^2-k^2}\tan[\sqrt{k_d^2-k^2}\,(h/2)]} + \frac{-(2k^2-k_s^2)}{2k^2\sqrt{k_d^2-k^2}\sqrt{k_s^2-k^2}} + \frac{(2k^2-k_s^2)^2}{8k^2\sqrt{k_d^2-k^2}\left(\sqrt{k_s^2-k^2}\right)^3}, \tag{9}$$

where j is the iteration number of the algorithm. After every iteration j, the new estimate of $k_s$ can be inserted back into equation (1) or (2) to test for convergence. This numerical process is applied to each specific Lamb wave at each measurement frequency and the result is an estimate of the square of the shear wavenumber. Finally, equation (3) is used to find the shear wavespeed.

Equations (1)-(8) illustrate that if the propagation wavenumber of any wave is known or can be measured with the dilatational wavespeed, the shear wavespeed can be estimated. That is, given k and $k_d$, the Newton-Raphson technique can be employed to solve for $k_s$. The process will be demonstrated with a numerical simulation and with experimental measurements.

The numerical simulation technique is first applied to a simulated data set created using a fully elastic three-dimensional model of the plate. The model is formulated from Naviers' equations of motion in an isotropic solid. By modeling the response as a sum of a dilatational component and a shear component, the general form of the solutions to the displacement fields are determined. Once these are known, they are inserted into the stress equations on free surfaces of the plate. In the chosen Cartesian coordinate system, the orientation is such that the xy-plane lies in the major dimensions of the plate and the z-axis is normal to the plate. On one side of the plate (z=0), the normal stress of the plate is set equal to the stress applied by a point forcing function and this corresponds to a mechanical shaker located at $x_0$ and $y_0$. This equation is written as $$\sigma_{zz}(x,y,0,t)=F_0\delta(x-x_0)\delta(y-y_0)\exp(i\omega t). \tag{10}$$

The other two shear stress boundary conditions at z=0 are set equal to zero, i.e., $$\sigma_{xz}(x,y,0,t)=0, \text{ and} \tag{11}$$

$$\sigma_{yz}(x,y,0,t)=0 \tag{12}$$

On the other side of the plate (z=h), all of the stress boundary conditions are zero, and these expressions are written as $$\sigma_{zz}(x,y,h,t)=0, \quad (13)$$

$$\sigma_{xz}(x,y,h,t)=0, \text{ and} \quad (14)$$

$$\sigma_{yz}(x,y,h,t)=0. \quad (15)$$

This produces a linear system of six equations that can be written in matrix form and consist of a dynamics matrix, an unknown coefficient vector, and a load vector. From this, the solution to the unknown constants can be determined. Finally, inserting these unknown values back into the displacement fields yields a known solution to the displacement fields in all three directions.

The simulation model corresponds to measurements of the normal velocity of the plate (at z=h) divided by the input force (at z=0) (the mobility of the system.) in the $k_x, k_y$ wavevector domain is written as $$\frac{W(k_x, k_y, \omega)}{F_0} = -X_1 i\alpha\omega\sin(\alpha h) + X_2 i\alpha\omega\cos(\alpha h) + X_3 k_y\omega\cos(\beta h) + X_4 k_y\omega\sin(\beta h) - X_5 k_x\omega\cos(\beta h) - X_6 k_x\omega\sin(\beta h), \quad (16)$$

where $k_x$ is wavenumber with respect to x-axis rad m$^{-1}$, $k_y$ is wavenumber with respect to the y-axis rad m$^{-1}$, i is $\sqrt{-1}$, and $$\alpha = \sqrt{k_d^2 - k_x^2 - k_y^2} \quad (17)$$

and $$\beta = \sqrt{k_s^2 - k_x^2 - k_y^2}. \quad (18)$$

The constants $X_1$ through $X_6$ are wave propagation coefficients and are determined by solving the three-dimensional elastic plate equation of motion when excited by a point force. It is noted here that geometrical shapes other than a plate will support different wave pattern responses.

To solve the propagation coefficients the dynamic model of the plate was developed for a system with no variation in the x-direction. Because the system described here has a point load (located at $x_0=0$ and $y_0=0$), the previous model is extended to include the variation in the x-direction, as well as retain the variations in the y- and z-directions. This theoretical development follows the previous model equations adding this additional degree of freedom.

The constants $X_1$ through $X_6$ are wave propagation coefficients and are determined by solving the matrix equation $$x = A^{-1} f, \quad (19)$$

where x is a 6×1 vector written as $$x = \{X_1 X_2 X_3 X_4 X_5 X_6\}^T, \quad (20)$$

the nonzero entry of the 6×1 vector f is $$f_1 = F_0, \quad (21)$$

and the nonzero entries of the 6×1 matrix A are $$a_{11} = -\lambda(\alpha^2 + k_x^2 + k_y^2) - 2\mu\alpha^2, \quad (22)$$

$$a_{14} = -2i\mu\beta k_y, \quad (23)$$

$$a_{16} = 2i\mu\beta k_x, \quad (24)$$

$$a_{22} = 2i\mu\alpha k_y, \quad (25)$$

$$a_{23} = -\mu(\beta^2 + k_x^2 - k_y^2), \quad (26)$$

$$a_{25} = -2\mu k_x k_y, \quad (27)$$

$$a_{32} = 2i\mu\alpha k_x, \quad (28)$$

$$a_{33} = \mu k_x k_y, \quad (29)$$

$$a_{34} = -\mu k_x k_y, \quad (30)$$

$$a_{35} = \mu(\beta^2 - k_x^2), \quad (31)$$

$$a_{36} = -\mu k_y^2, \quad (32)$$

$$a_{41} = -[\lambda(\alpha^2 + k_x^2 + k_y^2) + 2\mu\alpha^2]\cos(\alpha h), \quad (33)$$

$$a_{42} = -[\lambda(\alpha^2 + k_x^2 + k_y^2) + 2\mu\alpha^2]\sin(\alpha h), \quad (34)$$

$$a_{43} = 2i\mu\beta k_y \sin(\beta h), \quad (35)$$

$$a_{44} = -2i\mu\beta k_y \cos(\beta h), \quad (36)$$

$$a_{45} = -2i\mu\beta k_x \sin(\beta h), \quad (37)$$

$$a_{46} = 2i\mu\beta k_x \cos(\beta h), \quad (38)$$

$$a_{51} = -2i\mu\alpha k_y \sin(\alpha h), \quad (39)$$

$$a_{52} = 2i\mu\alpha k_y \cos(\alpha h), \quad (40)$$

$$a_{53} = -\mu(\beta^2 + k_x^2 - k_y^2)\cos(\beta h), \quad (41)$$

$$a_{54} = -\mu(\beta^2 + k_x^2 - k_y^2)\sin(\beta h), \quad (42)$$

$$a_{55} = -2\mu k_x k_y \cos(\beta h), \quad (43)$$

$$a_{56} = -2\mu k_x k_y \sin(\beta h), \quad (44)$$

$$a_{61} = -2i\mu\alpha k_x \sin(\alpha h), \quad (45)$$

$$a_{62} = 2i\mu\alpha k_x \cos(\alpha h), \quad (46)$$

$$a_{63} = \mu k_x k_y [\cos(\beta h) - \sin(\beta h)], \quad (47)$$

$$a_{64} = \mu k_x k_y [\sin(\beta h) - \cos(\beta h)], \quad (48)$$

$$a_{65} = \mu(\beta^2 - k_x^2)\cos(\beta h) - \mu k_y^2 \sin(\beta h), \quad (49)$$

and $$a_{66} = \mu(\beta^2 - k_x^2)\sin(\beta h) - \mu k_y^2 \cos(\beta h). \quad (50)$$

In the above equations, $\lambda$ and $\mu$ are the Lamé constants and are related to the wavespeeds by $$c_d = \sqrt{\frac{\lambda + 2\mu}{\rho}} \quad (51)$$

and $$c_s = \sqrt{\frac{\mu}{\rho}}, \quad (52)$$

where $\rho$ is the density of the plate (kg/m$^3$). Finally, the wavenumber in the plate is related to the $k_x$ and $k_y$ wavenumbers by $$\kappa = \sqrt{k_x^2 + k_y^2}. \quad (53)$$

When the response of the plate is at a wavenumber that corresponds to a Lamb wave, the propagation wavenumber equals the Lamb propagation wavenumber, i.e., $\kappa = k$.

Using equation (15), the mobility of the plate in the $k_x, k_y$ wavevector domain is simulated using a set of parameters that nominally corresponds to experimental values. These parameters are dilatational wavespeed of 1422 (1−0.05i) ms$^{-1}$, shear wavespeed of 220(1−0.05i) ms$^{-1}$, thickness of 0.0254 m, and density of 1100 kg/m$^3$. Note that the dilatational and shear wavespeeds are complex. This effect adds structural damping to the analysis that makes the simulation more realistic. Once the mobility fields are created (or later measured), they are searched so that the relative maximum of each Lamb wave propagating at a specific frequency is identified. From equation (53), a relative maxima for each specific wave in the $k_x,k_y$ wavevector domain can be modeled as a circle centered at $k_x=k_y=0$. Hence, a circular function was fit to the data sets of the relative maxima points. For each specific Lamb wave and fixed frequency, the radius of the circle was determined by the mean value of the radius of all of the individual points, via an ordinary least-square estimator. The resulting radius of the circle is the measured wavenumber k for the specific Lamb wave identified. Once known, either equation (5) (for symmetric waves) or equation (7) (for anti-symmetric waves) is used to estimate the square of the shear wavenumber $k_s^2$. From this, the shear wavespeed can be computed.

Figure 4:
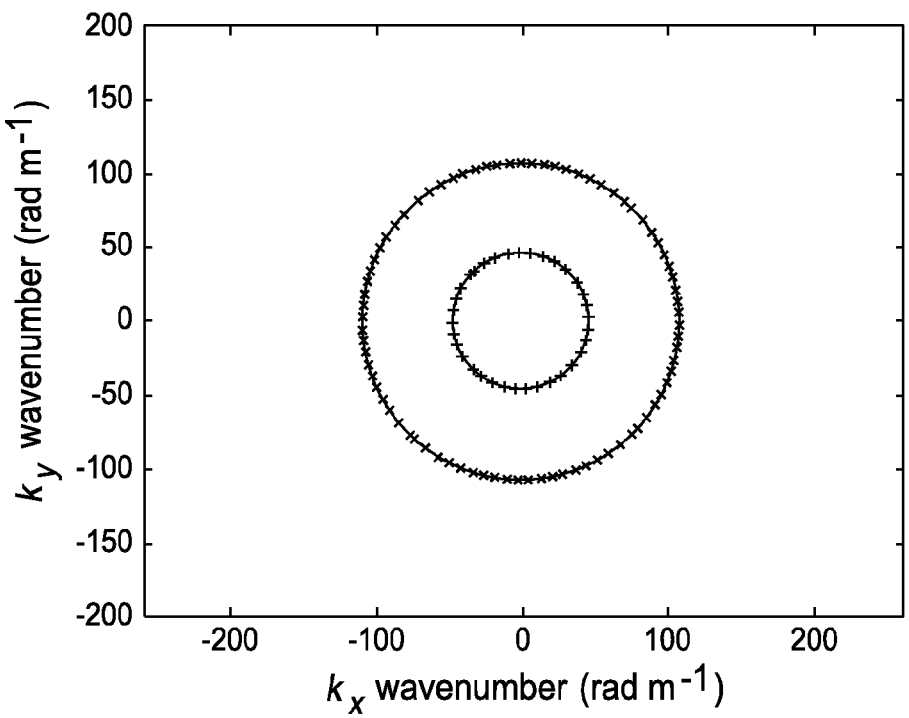
FIG. 4 is a plot of the theoretical wave propagation locations in the $k_x,k_y$ wavevector domain at 5 kHz.
Figure 5:
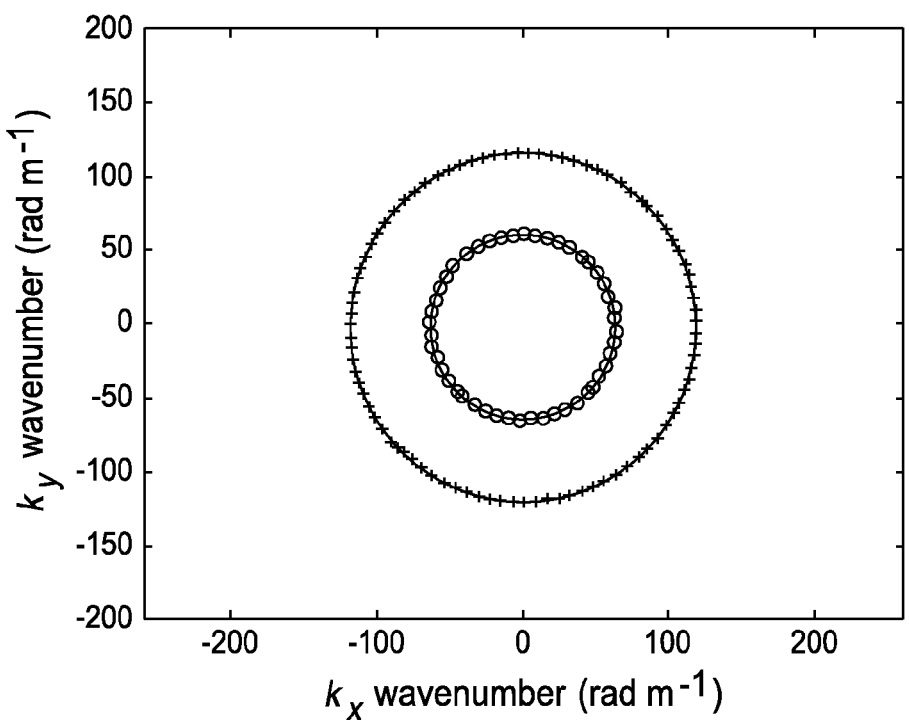
FIG. 5 is a plot of the experimental wave propagation locations in the $k_x,k_y$ wavevector domain at 5 kHz.

The simulation was conducted from 1-6 kHz in increments of 1 kHz. This can be conducted at any frequency above about 1 kHz. Below 1 kHz it has been found that standing waves occur. It is noted at this point that different authors use different terminology to identify individual Lamb waves in the wavevector-frequency (or wavenumber-frequency) plane. In this report, the work of J. D. Achenbach was used to define the names of each of the individual waves. FIG. 4 is a plot of the wave propagation locations in the $k_x,k_y$ wavevector domain at 5 kHz. The (first) flexural wave F(0) is denoted with an x, the longitudinal wave L(0) is denoted with a +, the (second) flexural wave FE(1) is denoted with an ○, and the circles fit to the markers are denoted with solid lines. For clarity, the markers have been decimated by 80%. Once the propagation wavenumbers are known, the shear wavespeed can be estimated using equation (1) for the symmetric L(0) longitudinal wave or equation (2) for the anti-symmetric F(0) and FE(1) flexural waves. The results of this simulation are shown in Table 1 of estimated shear wavespeeds for simulated waves for six frequency values. The average of the shear wavespeed estimate for the 11 simulated measurements was 220.5 ms$^{-1}$. It is noted that the addition of structural damping produces a slight biasing of the estimated shear wave values for each individual wave. When the damping value was set to 0, the estimation process produced an average value of 219.9 ms$^{-1}$, which varies slightly from the value of 220 ms$^{-1}$, and likely only due to discretization of the simulation in the wavevector domain.

TABLE 1

| Wave Name and Symmetry | Frequency f (kHz) | Simulated k (rad m$^{-1}$) | Estimated $k_s$ (rad m$^{-1}$) | Estimated $c_s$ (ms$^{-1}$) |
| --- | --- | --- | --- | --- |
| F(0) - Antisymmetric | 1 | 50.4 | 28.4 | 221.2 |
| F(0) - Antisymmetric | 2 | 79.5 | 56.8 | 221.3 |
| F(0) - Antisymmetric | 3 | 107.2 | 85.1 | 221.5 |
| F(0) - Antisymmetric | 4 | 134.5 | 113.1 | 222.1 |
| F(0) - Antisymmetric | 5 | 161.9 | 141.1 | 222.6 |
| L(0) - Symmetric | 3 | 46.4 | 87.0 | 216.7 |
| L(0) - Symmetric | 4 | 64.5 | 115.1 | 218.4 |
| L(0) - Symmetric | 5 | 86.8 | 143.0 | 219.7 |
| L(0) - Symmetric | 6 | 118.5 | 171.2 | 220.2 |
| FE(1) - Antisymmetric | 5 | 34.8 | 141.6 | 221.8 |
| FE(1) - Antisymmetric | 6 | 62.7 | 171.7 | 219.5 |

The initial estimate of the shear wavespeed is important for convergence of the algorithm. For the FE(1) flexural wave in a plate, the cut-on frequency can be approximated with $$f_1 \cong \frac{c_s}{2h}, \qquad (54)$$

where $f_1$ is the cut-on frequency (Hz) where the FE(1) wave propagation initiates at zero wavenumber. This simulation shows that the FE(1) wave does not exist at 4 kHz and does exist at 5 kHz, which produces a minimum shear wavespeed value of 203 ms$^{-1}$ and a maximum shear wavespeed value of 254 ms$^{-1}$ using equation (18). Based on these values, a convergence search using initial estimates from 170 ms$^{-1}$ to 270 ms$^{-1}$ was conducted.

As discussed in relation to FIG. 1, an experiment was undertaken to verify the proposed technique to measure shear wavespeed in a plate. The estimation process uses the following assumption: (1) The return energy from the reflections at the edge of the plate is not interfering with the measurement process, and (2) the particle motion is linear. A plate was molded using Cytech Industries EN-6, a two-part urethane that consists of a mixture of a prepolymer and a curing agent. The plate was 0.780 m by 0.755 m by 0.0254-m thick and weighed 16.6 kg. The dilatational wavespeed was previously measured at 1421 ms$^{-1}$. The plate was mounted on four corners with bungee cords and a Wilcoxon Model F3/Z602WA electromagnetic shaker was attached to the back near the middle. When the shaker was turned on, the front side was interrogated with a scanning Polytec LDV PSV-200 Doppler laser vibrometer that measured the normal velocity of the plate. The experiment was conducted at a room temperature of 15.5° C. A square grid of 90 by 90 points with a point-to-point spacing of 0.0082 m was used to collect 8100 spatial domain data points. After the data were collected, they were transformed into the frequency domain using a fast Fourier transform. Next, it was zero padded and transformed into the $k_x,k_y$ wavevector domain using a two-dimensional 512 by 512 point fast Fourier transform. Once this was accomplished, three Lamb waves were identified based on their relative maxima. Isotropic elastic plate theory predicts that every wave will be circular in the $k_x,k_y$ wavevector domain; thus, a circle was fit using an ordinary least-square estimate to the wavevector domain data. Measurements were made from 1 to 6 kHz in increments of 1 kHz.

Figure 6:
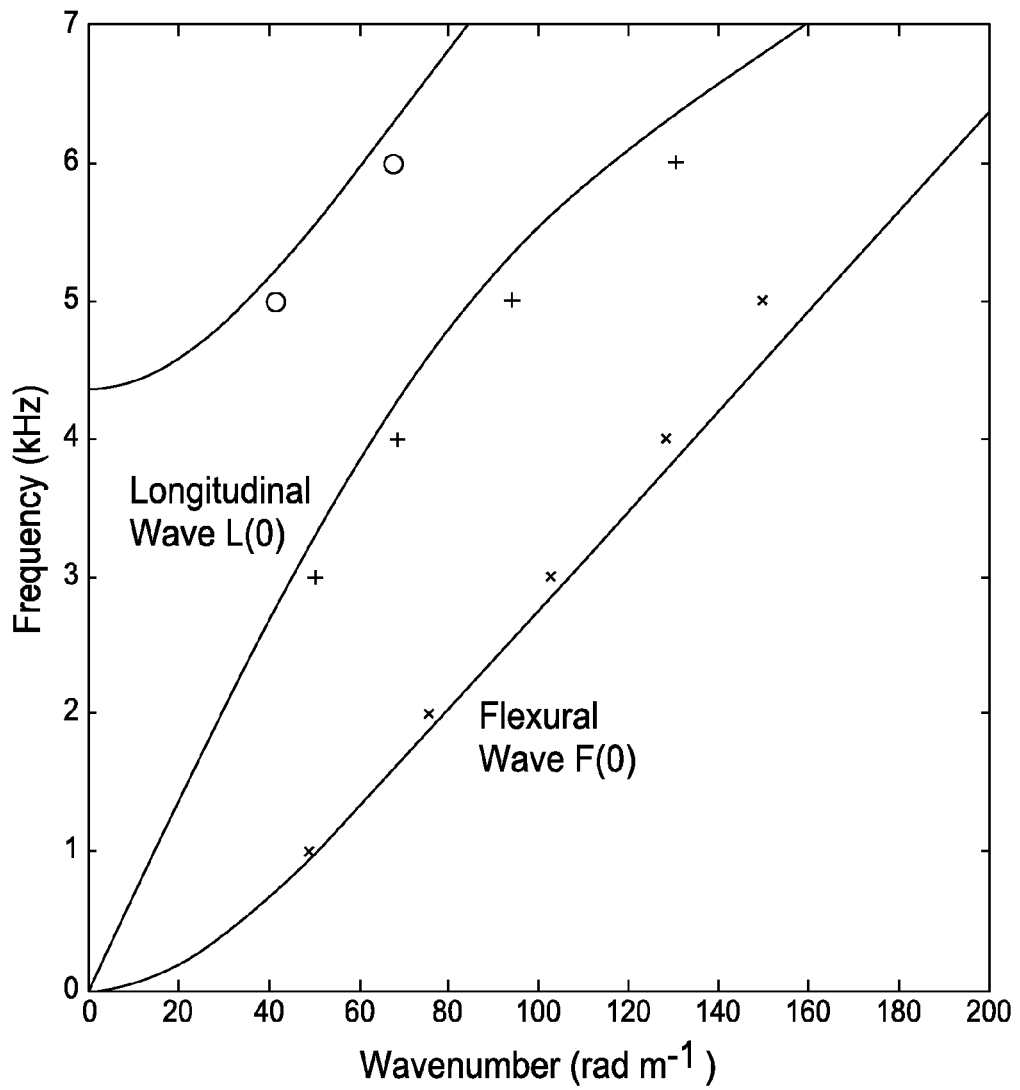
FIG. 6 is a dispersion curve in the wavenumber-frequency plane showing the experimental data points using discrete markers.

FIG. 6 is a plot of the wave propagation locations in the $k_x,k_y$ wavevector domain at 5 kHz. The F(0) flexural wave data are denoted with an "x", the L(0) longitudinal wave data are denoted with a "+", the FE(1) flexural wave is denoted with an "○", and the circles fit to the markers are denoted with solid lines. For clarity, the markers have been decimated by 80%. Once the propagation wavenumbers are known, the shear wavespeed can be estimated using equation (1) for the symmetric L(0) longitudinal wave or equation (2) for the antisymmetric F(0) and FE(1) flexural waves. Note, at the frequency of 5 kHz, the F(0) flexural wave is beginning to become incoherent across the major dimensions of the plate. The results of this estimation procedure are shown in Table 2 for all of the waves measured during the test and at all experimental frequencies.

TABLE 2

| Wave Name and Symmetry | Frequency f (kHz) | Simulated k (rad m$^{-1}$) | Estimated k$_s$ (rad m$^{-1}$) | Estimated c$_s$ (ms$^{-1}$) |
|---|---|---|---|---|
| F(0) - Antisymmetric | 1 | 49.2 | 26.5 | 229.9 |
| F(0) - Antisymmetric | 2 | 75.8 | 53.0 | 237.3 |
| F(0) - Antisymmetric | 3 | 103.0 | 80.7 | 233.6 |
| F(0) - Antisymmetric | 4 | 128.9 | 107.3 | 234.2 |
| F(0) - Antisymmetric | 5 | 150.3 | 129.2 | 243.2 |
| L(0) - Symmetric | 3 | 50.4 | 93.6 | 201.3 |
| L(0) - Symmetric | 4 | 68.9 | 121.3 | 207.1 |
| L(0) - Symmetric | 5 | 94.4 | 150.9 | 208.2 |
| L(0) - Symmetric | 6 | 131.0 | 180.0 | 209.5 |
| FE(1) - Antisymmetric | 5 | 41.7 | 148.4 | 211.8 |
| FE(1) - Antisymmetric | 6 | 67.8 | 177.8 | 212.0 |

The average value for the shear wavespeed estimate for the F(0) flexural wave was 235.6 ms$^{-1}$, the average shear wavespeed estimate for the L(0) longitudinal wave was 206.5 ms$^{-1}$, and the average value shear wavespeed estimate for the FE(1) flexural wave was 211.9 ms$^{-1}$. This indicates a mild dispersion of the shear wavespeed with respect to wave type. The average shear wavespeed for all measurements was 220.7 ms$^{-1}$. Using this average value and the value of the dilatational wavespeed, the dispersion curve in the wavenumber-frequency plane can be calculated. This is displayed as FIG. 6 along with each data point. The slight mismatch between theory and experiment is due to the variation of the shear wavespeed with respect to each individual wave.

Several parameters were varied to examine the accuracy of the measurement technique. First, the dilatational wavespeed was halved to 710.5 ms$^{-1}$ and then doubled 2840 ms$^{-1}$, which produced average shear wavespeed estimates of 224.1 ms$^{-1}$ and 220.0 ms$^{-1}$, respectively. This shows conclusively that the shear wavespeed estimate is relatively invariant to the dilatational wavespeed. Second, the thickness of the plate was thinned by 10% to 0.0229 m and thickened by 10% to 0.0279 m, and this produced average shear wavespeed estimates of 220.3 ms$^{-1}$ and 222.0 ms$^{-1}$, respectively. Finally, each of the measurements was statistically analyzed by calculating the standard deviation of the radius of the data points for each wave at every frequency. Once known, the shear wavespeeds were estimated at +1 and −1 standard deviation away from the mean. At −1 standard deviation, the average shear wavespeed was estimated to be 229.9 ms$^{-1}$, and for +1 standard deviation, the average shear wavespeed was estimated to be 213.0 ms$^{-1}$. These estimates are off by the original estimate of 220.7 ms$^{-1}$ by 4.4% and 3.3%, respectively, which generally indicates a stable estimation process.

The shear wavespeed of an isotropic plate can be accurately estimated using the measurement technique developed in this report. The approach consists of exciting the plate with a point force, measuring the normal component of velocity over its surface, and transforming the spatial measurements into the k$_x$,k$_y$ wavevector domain. The described technique is enabled by high-resolution wavevector measurement (via a scanning laser Doppler vibrometer). This fine resolution, coupled with zero padding within the k$_x$,k$_y$ spectra, allows for straightforward identification of propagating Lamb waves and their associated wavenumbers. An estimate of the shear wavespeed, using a Newton-Raphson method applied to the theoretical Rayleigh-Lamb plate equations, is straightforward. Numerical simulations and experimental measurements demonstrated that the method provides accurate estimates of the shear wavespeed, even when other measurement parameters have uncertainties. Nonconvergence of the Newton-Raphson method can occur, primarily due to poor initial estimates of the shear wavespeed, although this did not occur with the experimental data evaluated here.

It will be understood that many additional changes in the details, materials, steps and arrangement of parts, which have been herein described and illustrated in order to explain the nature of the invention, may be made by those skilled in the art within the principle and scope of the invention as expressed in the appended claims.

The foregoing description of the preferred embodiments of the invention has been presented for purposes of illustration and description only. It is not intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A method to measure a shear wavespeed of waves in an isotropic plate, comprising the steps of:
   providing the isotropic plate in a manner to minimize dynamic mounting forces;
   applying a time cyclical point force having a known frequency and magnitude to the plate to initiate waves in the plate;
   measuring normal velocity of the waves as a temporal domain measurement in a spatial domain on a first planar surface of the plate;
   transforming the temporal domain measurement into a frequency domain;
   transforming the frequency domain measurements into a {kx, ky} wavevector domain spectra using two Fourier transforms, one transform for each dimension, kx and ky;
   determining propagation wavenumbers for given Lamb waves from peaks within the {kx, ky} wavevector domain spectra; and
   determining a shear wavespeed of the waves in the plate by using the determined propagation wavenumbers, wherein propagation wavenumbers are determined by applying a Newton-Raphson gradient method to Raleigh-Lamb dispersion curve equations.

2. The method of claim 1 wherein said normal velocity of the waves is measured utilizing a scanning laser vibrometer.

3. The method of claim 1 wherein said time cyclical point force is applied at frequencies above about 1000 Hz.

4. The method of claim 1 wherein the step of determining a shear wavespeed is determined by:
   fitting a circle to the relative maxima points;
   determining the wavenumber k for a specific Lamb wave as a fitted radius of the circle;
   estimating the square of the shear wavenumber from the wavenumber; and
   computing the shear wavespeed from the square of the shear wavenumber.

5. The method of claim 4 wherein symmetric Lamb waves are used to estimate the square of the shear wavenumber.

6. The method of claim 4 wherein antisymmetric waves Lamb waves are used to estimate the square of the shear wavenumber.

* * * * *